United States Patent [19]
Vars
[11] 4,303,062
[45] Dec. 1, 1981

[54] THERAPEUTIC MAGNET

[75] Inventor: Charles A. Vars, Amherst, N.H.
[73] Assignee: InterVet, Inc., Milford, N.H.

[21] Appl. No.: 167,116
[22] Filed: Jul. 9, 1980
[51] Int. Cl.[3] ........................ A61B 19/00; A61N 1/42
[52] U.S. Cl. ...................................... 128/1.3; 128/356; 335/303
[58] Field of Search ................. 128/1.3, 356; 335/302, 335/303

[56] References Cited

U.S. PATENT DOCUMENTS

| | | | |
|---|---|---|---|
| 2,762,778 | 9/1956 | Gorter et al. | 252/62.5 |
| 2,812,203 | 11/1957 | Scholten | 292/251.5 |
| 2,844,363 | 7/1958 | Clark | 259/144 |
| 2,897,411 | 7/1959 | Brown et al. | 128/356 X |
| 3,005,458 | 12/1958 | Brook et al. | 128/356 |
| 3,079,535 | 2/1963 | Schultz | 317/201 |
| 3,187,239 | 6/1965 | Rosenberger et al. | 317/201 |
| 3,794,041 | 2/1974 | Frei et al. | 128/348 |
| 4,095,587 | 6/1978 | Ishikawa | 128/1.3 |
| 4,197,840 | 4/1980 | Beck | 128/76 R |

FOREIGN PATENT DOCUMENTS

| | | | |
|---|---|---|---|
| 2733982 | 2/1979 | Fed. Rep. of Germany | 128/1.3 |
| 93659 | 3/1969 | France | 128/1.3 |

*Primary Examiner*—Kyle L. Howell

[57] ABSTRACT

A therapeutic magnet for retention in the stomach of an animal comprises a plastic coated sintered ceramic magnet. The magnet is elongate and of uniform rectangular cross section in planes transverse to its principal dimension. The direction of magnetization is transverse to the principal dimension. The plastic coating serves to retain the separate parts of the magnet in the event of inadvertent fracture of the magnet.

3 Claims, 2 Drawing Figures

FIG. 1
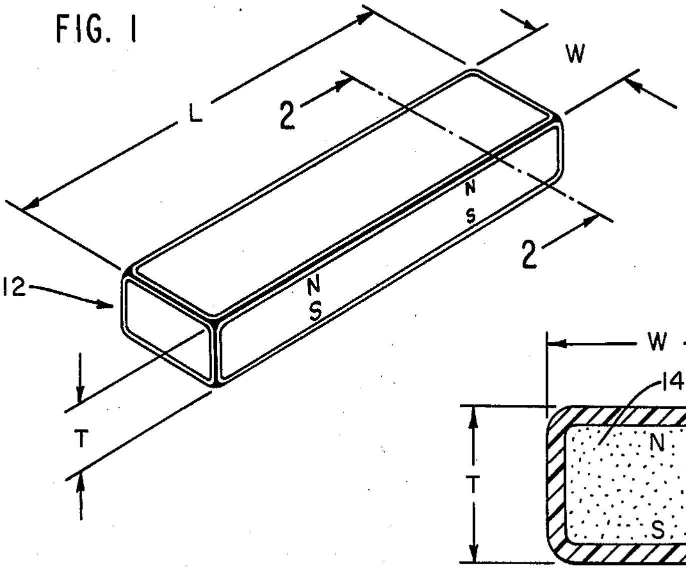
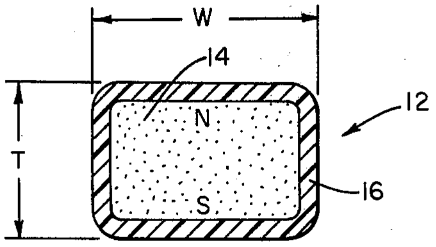
FIG. 2

THERAPEUTIC MAGNET

BRIEF SUMMARY

So-called "cattle magnets" have been in use for a number of years, a typical example being the type disclosed in U.S. Pat. No. 3,005,458 issued Oct. 24, 1961 to Brook et al. This patent discloses an uncoated magnet made of a metal alloy such as "'Alnico-V' or other non-corrosive material such as barium ferrite." The magnet is disclosed as being inserted in the second stomach or reticulum of a cow, where it remains to collect metal objects that the cow may ingest, such as nails, wire, staples or barbs. The magnet material is described as one that will not corrode in the cow's stomach. The patent describes a magnet having a particular "dog bone" shaped cross section defining grooves on two opposite sides that extend the length of the major dimension. This dimension also extends in the same direction as that of magnetization. Thus the patent states that the magnet has oppositely-poled ends, that it will tend to collect scrap metal along its length, and that the oppositely-poled ends will lessen the possibility that a sharp object will assume a position cross-wise to the groove, "a position that would increase the chance of stomach wall puncture."

Experience with the magnet described in the above patent over a number of years has been substantially satisfactory, in that the magnet is retained within the reticulum, once inserted, and efficiently collects metallic objects of many kinds. Because of its size the magnet remains in the central portion of the reticulum, picking up and retaining a variety of sharp metal objects, preventing them from becoming imbedded in the honeycomb lining of the stomach wall. Typically, the acids in the reticulum dissolve some of these objects in time; for example; a nail can be dissolved in approximately six months. In the meantime, these objects are retained in a position where they will not pierce the stomach wall as a result of inward force being applied to such wall by portions of the animal's body in movements such as lying down or returning to a standing position. However, care must be taken not to administer more than one such magnet to an animal, as two magnets attach themselves together side by side, that is, attach along their lengths from end to end with the south pole of one adjacent the north pole of the other, thus shunting one another and greatly reducing the external magnetic field.

The economics of using such magnets is a function of their cost. For example, "Alnico-V" is composed of iron, cobalt, nickel, aluminum and copper. Some of these components are imported from other countries and their availability must be considered. Cobalt, obtained principally from foreign countries, comprises approximately 24 parts per 100 of the composition of the alloy, and its cost has greatly increased over the years since the above patent issued. As a result of this and other material and fabrication price increases, the cost of an "Alnico-V" therapeutic magnet, using prices to distributors for purposes of comparison, has more than trebled between the date of the above patent and the present filing date.

A principal object of this invention is to provide a therapeutic magnet of materials more readily available and more simply fabricated than those materials hitherto deemed necessary for successful use.

The availability of alternative magnet materials has been considered to be limited by reason of certain commonly-held assumptions. For example, it has been assumed that to be useful any magnet would have to conform, not only in configuration, but also in magnetic polarization and functional characteristics, to the magnet of the above patent or to some other magnet hitherto proven to be effective in this application. Concerning the configuration, the size, shape and weight must be such as to permit the continued retention of the magnet within the reticulum; thus an elongate bar-like shape is selected. Concerning the magnetic polarization, the direction of polarization has substantial implications in that the total flux lines attainable in the external field is a function of the pole area and magnetic length as well as of the residual flux density or retentivity of the particular magnetic material. With the assumed elongate shape and physical dimensions of the magnet, it is necessary to select a material in which a sufficiently high external field can exist, as well as a material having a sufficiently high resistance to demagnetization. These considerations are further coupled with the necessity of using a non-corrosive material. When in addition to all of these considerations, it is further assumed that the magnet must have oppositely-poled ends, the field of choice of magnetic materials is substantially limited.

"Alnico-V," for example, has a residual flux density (also called "residual induction") of 12.8 kilogauss, and a coercive force of 600 to 640 oersteds which is a measure of resistance to demagnetization. A typical magnet of that material has an external field of 13,700 lines when in the configuration described in the above patent or up to 20,000 lines when in a simple cylindrical configuration with a diameter of $\frac{5}{8}$ inch. Many magnetic materials are ruled out by reason of having lower residual induction values, assuming that magnets of the same size, shape and magnetic orientation are to be fabricated.

The present invention represents a departure from the conceptual framework of the cited patent, characterized in part by the recognition based on further research and testing that transversely magnetized elongate magnets are not only workable for this therapeutic application, but also provide certain inherent advantages in terms of achieving adequate magnetic flux with a substantial number of readily available magnetic materials including sintered ceramic materials, previously regarded as unacceptable substitutes for "Alnico-V" or the like.

Another feature of the invention resides in the employment of a polymeric coating that envelops the magnet. This coating not only provides a durable non-corrosive covering, but also provides an additional function in the event of inadvertent chipping or breakage of the ceramic magnet. In such event the integrity of the coating is preserved, the magnet continues to be functional and the animal is protected from sharp or jagged edges that might be created by fracture of the magnetic material.

DESCRIPTION OF THE DRAWING

FIG. 1 is a perspective view of a preferred embodiment of the therapeutic magnet.

FIG. 2 is an elevation in section of the magnet taken on line 2—2 of FIG. 1 at right angles to its principal dimension.

DESCRIPTION

The drawings depict a preferred embodiment of the invention designated generally at 12. This comprises an integral body 14 of oriented sintered ceramic magnetic material with a coating 16 of polymeric material that completely covers the magnet. The thickness of the coating 16 is exaggerated in the drawing for purposes of description.

The magnet 14 is elongate, having a length L and having a cross section that is uniform throughout its length in planes perpendicular to the principal dimension L. The cross section comprises a width W and a thickness T. Preferably, the values of L, W and T are $2\frac{3}{4}$ inches, $\frac{3}{4}$ inch and $\frac{1}{2}$ inch, respectively, although some variation from these dimensions is possible provided that the size and shape are consistent with retention in the reticulum of the animal. Preferably, all edges and corners of the magnet 14 are slightly rounded as shown.

The composition of the magnet 14 preferably has the general formula $MO.6(Fe_2O_3)$, in which MO represents an oxide or oxides of one or more of the metals chosen from the group comprising barium, strontium and lead. A preferred material is sold commercially by the Arnold subsidiary of Magnetics & Electronics, Inc. under the trademark "Arnox 8."

At 20° C. "Arnox 8" has a typical residual induction or flux density as used in the oriented form of about 3.85 kilogauss and a coercive force of about 2900 oersteds. It is of interest to contrast these values with the previously stated values for "Alnico-V." The high coercive force of the ceramic magnet material is a measure of its relatively greater resistance to demagnetization as compared with the Alnico material.

As shown in each of the figures, the direction of polarization of the magnet 14 is at right angles to the principal dimension L, in contrast to the direction of magnetization described in the above-mentioned patent. The pole length corresponds to the value of T. It has been discovered that contrary to the inference from the patent, the transverse direction of magnetization does not result in an increase in the chance of stomach wall puncture, but does result in certain advantages. This was unexpected in view of the teaching of the patent that the magnet should have oppositely poled ends so that it would tend to collect scrap metal along its length; that is, so that a nail would most probably be drawn lengthwise against the magnet. Consistently with that approach, the magnet described in the patent was provided with lengthwise grooves into which the nail would be drawn.

However, magnets of the simpler, non-grooved shape and with the transverse polarization herein described have proven remarkably effective even with a reduction in the likelihood of an object such as a nail assuming a lengthwise position on the magnet. It has now been recognized that the principal efficacy of the magnet resides in the fact that it collects and retains metal objects, preventing them from becoming imbedded in the honeycomb lining of the stomach where the probability of piercing the stomach wall would be greatest. Thus the orientation of the objects on the magnet itself when adhering thereto is of comparatively less significance. In practice, a magnet with a number of objects such as nails, staples and the like adhering thereto remains within the central portion of the reticulum, in a position where incidental contact by any portion of the stomach lining has no material effect but to shift the relative positions of the more or less bunched objects around on the surfaces of the magnet.

The transverse direction of magnetic polarization has substantial significance in terms of enabling the use of ceramic materials which typically have substantially lower residual induction than "Alnico-V," for example, for this particular therapeutic application. This is because of the relationships that exist between the pole area, the magnetic length and the total external magnetic flux. Thus for an "Arnox 8" magnet as described above having dimensions L, W and T of $2\frac{3}{4}$ inch, $\frac{3}{4}$ inch and $\frac{1}{2}$ inch, respectively, the external field is 23,400 lines which exceeds that for either of the prior art magnets made of "Alnico-V," described above.

A further advantage that results from the transverse direction of magnetization is realized in cases where more than one magnet are administered to an individual animal. In this case, for example, two magnets will be paired by becoming attached along their lengths in either of two configurations: (1) with the south pole surface of one in contact with the north pole surface of the other, or (2) with their surfaces having the dimensions T and L in contact, the south pole surface of one being adjacent the north pole surface of the other. However, neither of these configurations reduces the external field as in the previously described case of paired "Alnico-V" magnets with oppositely poled ends.

As shown in FIG. 2, the magnet 14 is covered by a continuous coating 16. This coating is selected from among polymeric materials that are not degraded by the animal's stomach acids. An example is epoxy resin which may be coated on the magnet by clamping the magnet in a holder and immersing the holder in a fluidized bed of the resin.

In the event of inadvertent fracture of the ceramic magnet in use, the plastic coating 16 serves to retain the separate pieces, and for this purpose it is sufficiently thick and has sufficient tear strength to resist rupture. Thus the coating serves as a retainer, holding the separate ceramic fragments which may have sharp edges, preventing them from causing damage to the animal.

I claim:

1. A therapeutic magnetic bar for retention in the second stomach or reticulum of cattle, comprising an elongate magnet formed of a sintered material having the general formula $Mo.6 (Fe_2O_3)$, in which MO represents an oxide or oxides of one or more of the metals chosen from the group comprising barium, strontium and lead, said magnet being large enough for permanent retention in said second stomach, having a rectangular cross section in planes transverse to its principal dimension and being magnetized transversely to said dimension with its pole faces comprising the surfaces of greatest area, the length in said principal dimension being at least twice any one of the dimensions in said cross section, and a continuous polymeric coating enveloping said magnet and having a substantially uniform thickness and a tear strength sufficient to resist rupture in the event that said magnet is fractured.

2. The therapeutic magnetic bar of claim 1, in which said cross section is substantially uniform throughout said principal dimension.

3. A method of treating cattle for ingestion of ferrous metal objects, consisting of inserting into the second stomach or reticulum a bar comprising an elongate magnet formed of a sintered material having the general formula MO.6 ($Fe_2O_3$), in which MO represents an oxide or oxides of one or more of the metals chosen from the group comprising barium, strontium and lead, said magnet being large enough for permanent retention in said second stomach, having a rectangular cross section in planes transverse to its principal dimension and being magnetized transversely to said dimension, with its pole faces comprising the surfaces of greatest area, the length in said principal dimension being at least twice any one of the dimensions in said cross section, and a continuous polymeric coating enveloping said magnet and having a substantially uniform thickness and a tear strength sufficient to resist rupture in the event that said magnet is accidentally fractured.

* * * * *